United States Patent [19]
Soliman et al.

[11] Patent Number: 6,136,330
[45] Date of Patent: Oct. 24, 2000

[54] COMPOSITION

[75] Inventors: Nadia Soliman, East Brunswick; Zeenat F. Nabi, Cranbury, both of N.J.

[73] Assignee: Colgate Palmolive Company, New York, N.Y.

[21] Appl. No.: 09/183,524

[22] Filed: Oct. 30, 1998

[51] Int. Cl.⁷ ............................. A61K 7/00; A61K 7/48
[52] U.S. Cl. ......................... 424/401; 514/844; 514/846
[58] Field of Search ........................... 424/401; 514/844, 514/846, 847, 848

[56] References Cited

U.S. PATENT DOCUMENTS

| | | | |
|---|---|---|---|
| 5,646,321 | 7/1997 | O'Lenick, Jr. | 554/224 |
| 5,741,915 | 4/1998 | O'Lenick, Jr. | 554/52 |
| 5,741,916 | 4/1998 | O'Lenick, Jr. | 554/66 |
| 5,741,919 | 4/1998 | O'Lenick, Jr. | 554/224 |
| 5,770,751 | 6/1998 | O'Lenick, Jr. | 554/49 |
| 5,780,643 | 7/1998 | O'Lenick, Jr. | 548/350.1 |
| 5,786,388 | 7/1998 | O'Lenick, Jr. | 514/552 |
| 5,817,846 | 10/1998 | O'Lenick, Jr. | 554/224 |
| 5,834,516 | 11/1998 | O'Lenick, Jr. | 514/563 |
| 5,834,517 | 11/1998 | O'Lenick, Jr. | 514/563 |
| 5,907,049 | 5/1999 | O'Lenick, Jr. | 554/55 |
| 5,917,070 | 6/1999 | O'Lenick, Jr. | 554/224 |
| 5,919,958 | 7/1999 | O'Lenick, Jr. | 554/52 |
| 5,932,754 | 8/1999 | O'Lenick, Jr. | 554/52 |
| 5,972,322 | 10/1999 | Rath et al. | 424/70.11 |
| 5,993,792 | 11/1999 | Rath et al. | 424/70.28 |
| 6,013,818 | 1/2000 | O'Lenick, Jr. | 554/224 |

FOREIGN PATENT DOCUMENTS

| | | | |
|---|---|---|---|
| 0643960A1 | 9/1994 | European Pat. Off. | A61K 7/48 |
| WO 98/05294 | 2/1998 | European Pat. Off. | A61K 7/00 |
| XP002129399 | of 0000 | Japan . | |
| XP002129400 | of 0000 | Japan . | |
| XP002129401 | of 0000 | Japan . | |

OTHER PUBLICATIONS

Hoffman—La Roche, Inc., Vitamins & Fine Chemicals for Cosmetics, Mar. 8, 1996.

J. Am. Oil Chem. Soc., Damyanova et al, The Structure of the Triacylglycerols of Meadowfoam Oil, (1990), 67(8), 503–7.

J. Am. Oil Chem. Soc., Jolliff, Meadowfoam: New Source of Long–Chain Fatty Acids, (1987), 64(11), 1493–94.

*Primary Examiner*—Robert H. Harrison
*Attorney, Agent, or Firm*—Martin B. Barancik

[57] ABSTRACT

An aqueous liquid composition comprising:
a. a cleansing effective amount of a surfactant or mixture thereof;
b. an antioxidant effective amount of a material selected from the group consisting of vitamin E, vitamin C, vitamin A, a precursor of any of these said vitamins which is converted to the respective vitamin E, C and A when said precursor is contacted with skin, and mixtures thereof; and
c. a component b deposition enhancing effective amount of meadowfoam seed oil or derivative thereof

20 Claims, No Drawings

COMPOSITION

BACKGROUND OF THE INVENTION

Skin is continuously subjected to extremes of environmental stress and air pollution. Such insults can bring about generation of free radicals in skin which are a significant contributor to skin cell damage, premature aging of skin, skin cancer and the like. These free radicals are produced naturally in the body by such means as metabolic processes, lifestyle excesses, for example, such as exercise and the like as well as through exposure to environmental insults including ozone, heavy metals, halogenated hydrocarbons, ionization radiation and cigarette smoke.

It is generally accepted that materials having an antioxidant effect play a significant role against free radical induced skin damage. Key among these antioxidants are compounds commonly referred to as vitamins, particularly vitamins E, A and C. Since the human body is unable to synthesize its own Vitamin E it must be provided by extraneous sources, such as food and supplements. Recently, there have been attempts to deliver the vitamins to the skin from various skin cleansing and treatment compositions.

It has now been discovered that deposition of these vitamins and precursors upon skin can be substantially increased by the inclusion of meadowfoam oil or derivatives thereof within the composition. Such delivery is through an emulsion and provides an additional skin feel benefit through the presence of the oily emollient in the composition.

SUMMARY OF THE INVENTION

In accordance with the invention, there is an aqueous, liquid composition comprising:

(a) at least about 1 wt % of a surfactant and mixtures thereof;

(b) about 0.01 to about 2.0 wt % of a material selected from the group consisting of vitamin E, vitamin C, vitamin A, a precursor of any of these said vitamins which is converted to the respective vitamin E, C and A when said precursor is contacted with skin, and mixtures thereof;

(c) a skin deposition enhancing effective amount of a compound selected from the group consisting of meadowfoam seed oil, meadowfoam seed oil glyceride, meadowfoam seed oil ester, meadowfoam seed oil betaine and meadowfoam seed oil alkanolamides.

DETAILED DESCRIPTION OF THE INVENTION

In line with the cleansing activity of the composition, there must be a skin cleansing effective amount of a surfactant present in the composition. Soap, a long chain alkyl or alkenyl, branched or normal carboxylic acid salt such as sodium, potassium, ammonium or substituted ammonium salt, can be present in the composition as an example of an anionic surfactant. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Because of its potential harshness soap is not a preferred surfactant and can be omitted from the composition.

Other surfactants can be present in the composition as well. Examples of such surfactants are the anionic, amphoteric, nonionic and cationic surfactants. Examples of anionic zwitterionic surfactants include but are not limited to soaps, alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates, the reaction product of fatty acids having from 10 to 22 carbon atoms esterified with isethionic acid and neutralized with sodium hydroxide, water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

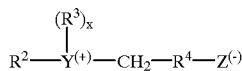

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecyiammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecylphosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate;

4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-aikyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;

dodecyltrimethylammonium chloride;

nonylbenzylethyldimethyl ammonium nitrate;

tetradecylpyridinium bromide;

laurylpyridinium chloride;

cetylpyridinium chloride laurylpyridinium chloride;

laurylisoquinolium bromide;

ditallow(Hydrogenated)dimethyl ammonium chloride;

dilauryldimethyl ammonium chloride; and stearalkonium chloride.

Additional cationic surfactants are disclosed in U.S. Pat. No. 4,303,543 see column 4, lines 58 28 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$R_1R_2R_3N \rightarrow 0$ wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$RR'R''P \rightarrow 0$ wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyidimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 21 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about I to about 3, preferably about 1.3 to about 2.0.

The quantity of surfactant to be employed in the composition is not unduly significant. It should generally be sufficient to exert a cleansing effect upon skin. Generally, a minimum of about 1 wt % of the composition can be a surfactant or mixtures thereof. Preferably about 2, 3, 4 or 5 wt % can be employed as a minimum. A maximum of about 30 wt % of the composition can be a surfactant or mixture thereof, preferably a maximum of about 25, 20 or 18 wt % can be employed. Generally at least about 20 wt % of surfactant present is an anionic surfactant or mixture thereof, preferably a mild anionic surfactant. Usually, the anionic surfactant or mixture thereof is at least about 30 or 40 wt % of the surfactant present. Soap need not be present. Any specific surfactant or group of surfactants, i.e. amphoteric, zwitterionic, nonionic and cationic can individually or in groups be omitted.

The vitamins which have antioxidant effects include E, C and A. Generally, it is preferred to use a derivative of the actual vitamin since the vitamins per se are somewhat unstable in comparison to various derivatives, particularly in an aqueous liquid composition. When in contact with skin, these vitamin derivatives are converted to the vitamin per se so it can exert its antioxidant effect. For example, vitamin E, a tocophenol, is utilized in compositions preferably as the methyl ester which is then bioconverted to vitamin E in the skin. In a similar manner, Vitamin A is utilized in the composition as a palmitate ester, for example, which is then bioconverted by skin to its antioxidant effective moiety, vitamin A. Any precursor which is connected by a skin containing system to the active vitamin antioxidant can be employed in the composition. For example, esters of the vitamins can be employed as effective precursors. Examples of effective esters are those having about 1 to about 20 carbon atoms, for example, the methyl, propyl, hexyl, decyl, lauryl, palmityl and behenyl ester of the vitamin such as the methyl ester of vitamin E or the palmitate ester of vitamin A. Of the actual vitamins the alpha tocopherol compound is preferred as vitamin E. Similar precursors can be used for vitamin C.

The vitamin or vitamin precursor and mixture thereof can be present in the composition in quantities of at least about 0.01 wt %, or generally about 0.1, 0.2, or about 0.5 wt %. Lesser amount of vitamin A or precursor can be present as opposed to vitamin E or precursor. Maximum quantities of vitamin or precursor generally do not exceed about 2.0 wt % of the composition, or generally about 1.5 or 1.0 wt % of the composition.

The proper integration of the vitamin or precursor in the liquid aqueous composition is highly significant for its performance as an antioxidant, skin protecting material. The vitamin or precursor must be sufficiently solubilized in the composition so as to be compatible not separate into a second phase, and not cause unfavorable interactions amongst the other composition components to any great extent. However, it must still be available for ready deposition upon the skin during the time the composition is in contact with the skin. It has been found that the long chain alkyl or alkenyl mono and di alcohol amides are surprisingly effective. These materials at a concentration generally below about 2 wt %, preferably below about 1.5 wt % of the composition solubilize the vitamin or precursor, particularly the methyl ester of Vitamin E and the palmitate ester of Vitamin A. They are compatible with the overall composition and permit deposition of effective levels of vitamins or precursors on the skin. Any minimum level of amide which permits these occurrences can be employed. However, generally a minimum of about 0.2 wt % of the liquid, aqueous composition, preferably a minimum of about 0.5 wt % of the composition can be employed.

In order for the antioxidant material to properly protect skin from free radical attack, it must be properly deposited. It has now been found that meadowfoam seed oil and its derivatives are particularly able in promoting deposition. The meadowfoam seed oil is commonly found in native state in Limnanthes Alba as the triglyceride with fatty acids being a mix of alkenoic fatty acids, mostly $C_{20}$, i.e., 5-eicosenoic acid, others being $C_{21}$ i.e., 5,13-heneicosenoic acid while still others being a mix of $C_{22}$, i.e., 5-docosenoic acid and $C_{22}$, i.e. 13-docosenoic acid.

Various issued patents have disclosed the meadowfoam seed oil constituents and its derivatives in a more detailed manner, e.g. U.S. Pat. Nos. 5,646,321; 5,741,915; 5,741,916; and 5,741,919 incorporated by reference wherein the following structure and quantities are mentioned.

The fatty distribution of the oil ranges from 20 to 22 carbons and has unsaturation in specific locations. The oil contains 97% by weight higher unsaturated alkyl groups. Typically, meadowfoam oil is believed to contain 60–65% of a twenty carbon terminal mono-carboxy acid having one unsaturation between carbon 5 and 6. Additionally, it contains 12–20% of a twenty two carbon terminal mono-carboxy acid having one unsaturation between carbon 5 and 6, and 15–28% of a twenty two carbon terminal mono-carboxy acid having one unsaturation between carbon 5 and 6, an another between carbon 13 and 14. These are shown below structurally.

60–65% by weight HOOC—$(CH_2)_3$—CH=CH—$(CH_2)_{13}$—$CH_3$

12–20% by weight a mixture of

HOOC—$(CH_2)_3$—CH=CH—$(CH_2)_{15}$—$CH_3$ and

HOOC—$(CH_2)_{11}$—CH=CH—$(CH_2)_7$—$CH_3$ and

15–28% by weight

HOOC—$(CH_2)_3$—CH=CH—$(CH_2)_6$—CH=CH—$(CH_2)_6$—$CH_3$

Meadowfoam seed oil can also be present in its glyceride form.

Derivatives of the meadowfoam oil carboxylic acids can be used in the compositions of this invention as well as the long chain carboxylic acids depicted above. These involve performing standard chemistry on the carboxy group while maintaining the unsaturation untouched or at least essentially untouched. Examples of such derivatives are the esters, for example, as disclosed in U.S. Pat. Nos. 5,741,919 and 5,646,321; the alkanolamides, for examples, as disclosed in U.S. Pat. No. 5,741,916 and the betaines derivatives, for example, as disclosed in U.S. Pat. No. 5,741,915. The meadowfoam oil carboxylic acids or derivatives thereof can be used in the composition at deposition enhancing quantities, generally a minimum of about 0.5 wt % or about 1.0 or 2.0 wt %. A maximum quantity is generally no higher than about 6 wt %, or preferably about 5 or 4 wt % of the composition.

When employing meadowfoam seed oil and/or its derivative(s), the deposition onto skin of the antioxidant vitamins and precursors is substantially higher than when no meadowfoam seed oil or derivative is present.

Deposition is also enhanced by the presence of cationic polymers.

The viscosity of the compositions can vary from about 1,000 to about 60,000 centipoise. This is from a low viscosity rinse off composition to a high viscosity lotion or cream. With respect to a rinse off composition, the viscosity is generally from about 1,000 to about 15,000, preferably about 2,000 to about 12,000 centipoise as measured at about 25° C. on a Brookfield RVTD viscometer using a spindle number 5 at 20 rpm. For the more viscous formulations, a T-bar "spindle" is employed, number C at 3 to 5 rpm. Generally, the compositions have a pH of about 4.5 to 7, preferably a pH of about 5 to 6.5 or about 5 to 6.

The composition can take the form of a "rinse-off" cleansing composition. It can also be applied as a "leave-on" cream or a lotion. The "rinse-off" composition is preferred since a significant quantity of vitamin can actually be deposited on the skin during the cleansing procedure. The rinse off cleansing formulation can be prepared in the usual manner known to the art. However, it is preferable to add the amide with the vitamin or precursors as well as the meadowfoam seed oil and/or its derivatives prior to contact with the remainder of the composition. A typical preparation follows.

In a main vessel at room temperature, PQ-10 is dispersed in water which is then heated to 50–60° C. Then, to this main vessel at 50–60° C. are added various water soluble ingredients, for example, cocoamidopropylbetaine, decylpolyglucoside, sodium laureth-2-sulfate, glycerin and polyquat 7 one-by-one with adequate mixing while minimizing aeration. A temperature of about 50–60° C. is maintained. In a separate vessel, Methocel E-4M, a hydroxypropyl methyl cellulose, if present, is dispersed in water heated to about 80° C. When well dispersed, the Methocel is added to the main vessel. In a further separate vessel, the oil phase components CDEA, lauric acid, PEG-15 stearmonium chloride, vitamin E acetate and meadowfoam seed oil are added with appropriate mixing and heated to 50–60° C. When this "oil phase" is homogeneous, it is added to the main vessel at about 60° C. As the mixture thickens, increase mixing speed to provide homogenous mixture while minimizing aeration. It is then mixed for about 10–20 minutes at about 50–60° C. The batch is then cooled gradually to about 35–40° C. In a separate vessel, pre-mix remaining CDEA with vitamin A palmitate until uniform. The vitamin pre-mix is added to the main batch and mixed well at about 35° C. The various minors such as fragrance and preservative added to the main vessel and mixed at 35°.

Below are examples of the invention. Those examples are intended to exemplify the broad nature of the inventive concept and not be unduly limiting thereof. Also included are comparative examples showing the advantages of the invention.

EXAMPLE 1

A preferred composition is 12 wt % sodium laureth-2-sulfate, 3 wt % CAPB, 2.5 wt % decyl polyglucose, 2 wt % glycerine, 2 wt % lauric acid, 3 wt % meadowfoam seed oil (limnanthes albe), 1 wt % vitamin E acetate, 1 wt % CDEA, 0.3 wt % PEG-15 stearmonium chloride, 0.2 wt % hydroxypropylmethylcellulose, 0.2 wt % polyquat 10, 0.2 wt % polyquat 7, 0.01 wt% vitamin A palmitate with tocophenol, preservative, and the balance water. The composition has a pH of about 5.5 and a viscosity at room temperature using a RVTD viscometer with a number 5 spindle at 20 rpm of 13,000 centipoise.

EXAMPLE 2

In vitro/Porcine Skin Deposition Comparison Results

Porcine (pig) skin samples are cut (1.25×1.25 inch) and stored at −20° C. freezer. On the day of experiment, the pig skins are thawed for 45 minutes (water is sprayed from a squirt bottle periodically to prevent dehydration). The skin samples are set on a deposition chamber as described in U.S. Pat. No. 4,836,014 (P. Hilliard) issued 1989 and the screws tightened firmly. The shower gel (100 $\mu$l) as applied to each skin sample, rubbed gently with a glass rod for 15 seconds, and equilibrated for 45 seconds. The shower gel solution is then removed and the skin washed 10 times with water. Each time the chamber is filled up to the rim with water. The water is removed with a pipette tip attached to a vacuum. The deposited materials are extracted with 1 ml ethanol for one minute. The process is repeated 3 times. The pooled ethanol extracts are evaporated to dryness under $N_2$ and stored at −20° C. To analyze the vitamin contents by HPLC the dried material is resuspended in a 0.5 ml solution of methanol:isopropanol:butanol (70:20:10).

The HPLC conditions were:

Column=100 mm Phenomenex Ultracarb 5u-ODS 20

Mobile phase=75 methanol/20 isopropanol/5 butanol

Flow rate 0.75 ml/min.

Wave length was 288 mm.

Under these conditions, retention times for the vitamins were:

Vitamin E=5.0 and Vitamin E acetate=7.0 min. approximately.

Various compositions were tested for Vitamin E acetate deposition utilizing the base composition of Example 1 with or without certain material and certain procedure of addition. The vitamin being post-added means the last step after forming the emulsion. If not post-added, the vitamin is processed with the meadowfoam oil. The vitamin E acetate deposition is measured in $\mu g/cm^2$ of skin.

| Example | Meadowfoam Oil | Vitamin Post-Added | Methocel | Deposition $\mu g/cm^2$ |
|---|---|---|---|---|
| A | No | Yes | No | 0.52 |
| B | Yes | Yes | No | 0.65 |
| C | Yes | No | No | 1.36 |
| D | Yes | No | Yes 0.2 wt % | 2.15 |

The results are clear. The order of addition of the vitamin is critical to results. Merely adding the vitamin to the finished formulation significanty affects the deposition of vitamin onto the skin. By adding the vitamin with the meadowfoam oil, as opposed to at the end of the formulation preparation, the amount of vitamin deposition is doubled, Example C compared to Example B. Interestingly, when a stabilizing thickener is additionally present, hydroxypropyl methylcellulose, the deposition is increased an additional 58%. Other hydroxyalkyl celluloses, methylated or not can be used, for example, hydroxyethyl cellulose, hydroxyethyl methyl cellulose, hydroxypropyl cellulose and the like. Any deposition enhancing quantity can be employed, although generally at least about 0.05 is employed, preferably at least about 0.1 wt % of the composition. Generally, no more than about 1.0 wt % is employed, usually no more than about 0.5 wt % of the composition.

EXAMPLE 3

In vitro and In vivo test protocols and results showing efficacy of vitamin and vitamin recursors in protecting against free radical attack on skin (antioxidant activity).

In Vitro

To measure the antioxidant benefits of various formulations are applied to skin equivalent modes (Epiderm™) purchased from MatTek. After 1 minute of contact, skin samples are rinsed with phosphate buffered saline (PBS), and incubated in a maintenance medium for 3 hours to allow the bioconversion of the provitamin. Cumene hydroperoxide was added to the stratum corneum (sc) surface. Cumene peroxide-induced cell cytotoxicity and the protection by the formulations are analyzed by MTT or Alamar blue assay.

The MTT assay uses 3-[4,5-dimethylthiazol-2-yl]-2,5-diphenyltetrazolium bromide (MTT-reduction assay). MTT solution is prepared as 0.5 mg/ml in phosphate buffered saline just before use and filtered through a 0.22 μm filter. MatTek EpiDerm skins are placed in 24 well tissue culture plates and 500 μl of the MTT solutions are added to each well and incubated at 37° C. for 4 hours. The cell survivability is analyzed by measuring the ability of the cells mitochondria to reduce the colorless MTT to a colored formazan(crystals) end product. The reaction is terminated by the removal of the MTT solution. Addition of 500 μl of 0.04N HCl in isopropanol to each well is used to dissolve the intracellular MTT formazan crystals. The contents of each well are mixed gently in an orbital shaker at room temperature for 2 hours and the absorbency at 570 nm is measured by an ELISA reader (Titertek, Multiscan, MC).

In Vivo

To measure the antioxidant benefits of the formulations, human forearms are washed with the formulation for 1 minute (30 second lather, 30 second waiting, and 15 second rinse). Three hours after the wash, skin samples are collected with tapes. Alkyl peroxide (cumene hydroperoxide) was added to the stratum corneum side of the tape. Neutralizing efficacy or antioxidant benefits of formulations are identified by measuring the remaining cumene hydroperoxide on the stratum corneum. This is measured by LPO (lipid peroxide) assay kit (Kamiya Biomedical Company, Seattle, Wash.) utilizing the directions therein.

The LPO assay is performed using Determiner® LPO kit (Kamiya Biomedical Company, Wash.). The kit utilizes hemoglobin to catalyze the transfer of an oxidizing equivalent from the lipid hydroperoxide to a colorless derivative of methylene blue, forming a colored compound which can be measured spectrophotometrically. A 20 μl sample of tissue extract is added to a microfuge tube containing 250 μl of reagent-1; after vortex mixing, the solution is incubated for 5 minutes at 30° C. 500 μl of Reagent-2 is added. The reaction mixture is vortex mixed again, and incubated at 30° C. for 30 minutes. The samples are then centrifuged at 800× g for 6 minutes to remove tissue debris. The absorbency of the supernatant is measured at 674 nm in a spectrophotometer.

| Results | | |
|---|---|---|
| | % Protection | |
| Sample | In Vitro | In Vivo |
| Placebo without vitamin or vitamin precursor or meadowfoam oil* | 0 | 5 |
| Example 1 with no post addition and 0.2 wt % Methocel | 75 | 35 |

*Placebo is 11.2 wt % ammonium lauryl sulfate, 1.5 wt % cocoamidopropylbetaine, 1 wt % cocodiethanolamide, 0.12 wt % polyquat 7 and the balance water.

What is claimed is:

1. An aqueous liquid composition comprising a. a cleansing effective amount of a surfactant or mixture thereof, b. an antioxidant effective amount of a material selected from the group consisting of vitamin E, vitamin C, vitamin A, a precursor of any of these said vitamins which is converted to the respective vitamin E, C and A when said precursor is contacted with skin, and mixtures thereof, and c. a component b deposition enhancing effective amount of meadowfoam seed oil or derivative thereof.

2. The composition in accordance with claim 1 wherein component a is present in at east about one weight percent of the composition.

3. The composition in accordance with claim 1 wherein component b is present in at least about 0.01 wt % of the composition.

4. The composition in accordance with claim 1 wherein the surfactant is anionic.

5. The composition in accordance with claim 1 wherein at least about 2 wt % of the composition is a surfactant.

6. The composition in accordance with claim 1 wherein the material is vitamin A.

7. The composition in accordance with claim 1 wherein the material is a vitamin A precursor which is converted to vitamin A when contacted with skin.

8. The composition in accordance with claim 1 wherein the component c compound is at least about 0.05 wt % of the composition.

9. The composition in accordance with claim 1 wherein the material is vitamin E.

10. The composition in accordance with claim 1 wherein the material is a vitamin E precursor which is converted to vitamin E when contacted with skin.

11. The composition in accordance with claim 1 wherein the component c is meadowfoam seed oil carboxylic acid or meadowfoam seed oil glyceride.

12. The composition in accordance with claim 11 wherein the material is the palmitate ester of vitamin A.

13. The composition in accordance with claim 11 wherein the material is the methyl ester of vitamin E.

14. The composition in accordance with claim 13 wherein the material is the methyl ester of alpha tocopherol.

15. The composition in accordance with claim 1 wherein additionally present in the composition is a component b deposition enhancing amount of a cellulose polymer.

16. The composition in accordance with claim 15 wherein the polymer is hydroxy propyl or hydroxy ethyl cellulose.

17. The composition in accordance with claim 15 where the polymer is a methyl cellulose.

18. The composition in accordance with claim 17 wherein the polymer is hydroxyethyl or hydroxypropyl methyl cellulose.

19. The composition in accordance with claim 18 wherein the polymer is hydroxypropylmethyl cellulose.

20. The composition in accordance with claim 1 wherein the composition is a rinse off composition.

* * * * *